(12) United States Patent
Seto et al.

(10) Patent No.: US 7,612,981 B2
(45) Date of Patent: Nov. 3, 2009

(54) ION GENERATOR AND NEUTRALIZER

(75) Inventors: Takafumi Seto, Tsukuba (JP); Makoto Hirasawa, Tsukuba (JP); Yasufumi Hozumi, Tsukuba (JP); Masaaki Tsuji, Tsukuba (JP); Akira Okuyama, Tokyo (JP); Susumu Saito, Tokyo (JP)

(73) Assignees: National Institute of Advanced Industrial Science & Technology, Tokyo (JP); FISA Corporation, Tokyo (JP)

( * ) Notice: Subject to any disclaimer, the term of this patent is extended or adjusted under 35 U.S.C. 154(b) by 146 days.

(21) Appl. No.: 12/010,928

(22) Filed: Jan. 31, 2008

(65) Prior Publication Data

US 2008/0191146 A1 Aug. 14, 2008

(30) Foreign Application Priority Data

Feb. 9, 2007 (JP) .......................... P2007-030524

(51) Int. Cl.
*H01T 23/00* (2006.01)
*G03G 15/02* (2006.01)
*H05F 3/00* (2006.01)

(52) U.S. Cl. ...................................... 361/230; 361/235
(58) Field of Classification Search ............. 250/423 R, 250/426; 313/359.1, 230; 361/213, 230, 361/231, 235
See application file for complete search history.

(56) References Cited

U.S. PATENT DOCUMENTS

| | | | | |
|---|---|---|---|---|
| 6,252,233 B1 * | 6/2001 | Good | ...................... | 250/423 R |
| 7,254,006 B2 * | 8/2007 | Sekoguchi et al. | .......... | 361/230 |
| 7,256,979 B2 * | 8/2007 | Sekoguchi et al. | .......... | 361/231 |
| 7,485,265 B2 * | 2/2009 | Park et al. | .............. | 422/186.04 |
| 2004/0145853 A1 * | 7/2004 | Sekoguchi et al. | .......... | 361/225 |
| 2004/0201946 A1 * | 10/2004 | Iwamatsu | .................... | 361/230 |
| 2005/0168907 A1 * | 8/2005 | Sekoguchi et al. | .......... | 361/230 |

(Continued)

FOREIGN PATENT DOCUMENTS

JP 04094099 A * 3/1992

(Continued)

*Primary Examiner*—Jack I Berman
*Assistant Examiner*—Brooke Purinton
(74) *Attorney, Agent, or Firm*—Roylance, Abrams, Berdo & Goodman, L.L.P.

(57) ABSTRACT

The present invention is relating to an ion generator and an ionizer, in which the ion generator can obtain stable ion generation even if the electrode and the power supply slightly change, satisfies voltage and frequency conditions for realizing an ozone concentration less than 50 ppb as an allowable concentration. The ion generator of the present invention is characterized as a fan-type ion generator including a dielectric body, a discharge electrode having fine protrusions arranged on the surface of this dielectric body, and an induction electrode arranged on the back surface of the dielectric body, comprising: an ion element in which by applying a sinusoidal AC high voltage to the discharge electrode, a potential difference from the induction electrode is generated, plasma is formed on the surface of the dielectric body, and positive ions, negative ions, and ozone are produced according to air ionization; and a fan which generates an airflow with respect to the discharge electrode, wherein the peak-to-peak voltage is not less than 3.5 kV and not more than 7 kV, the frequency f, and the relationship between the voltage V and the frequency f satisfies a specific parameter. And, the ionizer of the present invention is characterized that ionization is performed by using the above mentioned fan-type ion generator.

3 Claims, 7 Drawing Sheets

U.S. PATENT DOCUMENTS

| | | | |
|---|---|---|---|
| 2006/0024219 A1* | 2/2006 | Park et al. | 422/186.04 |
| 2006/0056130 A1* | 3/2006 | Kim et al. | 361/230 |
| 2006/0227493 A1* | 10/2006 | Kim et al. | 361/231 |
| 2007/0109711 A1* | 5/2007 | Sekoguchi et al. | 361/230 |

FOREIGN PATENT DOCUMENTS

| | | | |
|---|---|---|---|
| JP | 08082980 A * | 3/1996 | |
| JP | 2003249327 A * | 9/2003 | |
| JP | 2004234972 A * | 8/2004 | |
| JP | 2006059711 A * | 3/2006 | |
| JP | 2006196291 A * | 7/2006 | |
| JP | 2006222019 A * | 8/2006 | |
| JP | 2006260963 A * | 9/2006 | |
| WO | WO 2004109875 A1 * | 12/2004 | |

* cited by examiner (A)              (B)

ION GENERATOR AND NEUTRALIZER

BACKGROUND OF THE INVENTION

1. Field of the Invention

The present invention relates to an ion generator which generates air ion clusters and an ionizer which removes static electricity on an object surface, and more specifically, to an ion generator and an ionizer having regulated design ranges of voltage, frequency, and airflow rate for efficient generation and conveyance of ions by a plate-like ion generating element.

2. Description of the Background Art

Among conventional general ion generators and ionizers, for example, in the case of a conventional ionizer, corona discharge is caused by applying a high voltage by a high-voltage power supply to a pointed-needle-like ion generating electrode, whereby the air is ionized (for example, refer to Patent Document 1). The needle-like ion generating electrode must form a local electric field at its tip end portion for forming plasma according to air ionization, and its voltage is 5 to 7 kV or more in the case of using a DC high voltage power supply. Therefore, to generate a sufficient amount of ions by applying a DC voltage to the needle electrode, much power is consumed, and the power supply unit inevitably increases in size.

Some of the power supplies for applying a high voltage to be applied to the needle-like ion generating electrode use a piezoelectric transformer for the purpose of downsizing of the device and control of the ion balance, and the voltage thereof is about 2 to 3 kV, and the frequency is 20 to 100 kHz (refer to Patent Document 2). In other words, to downsize the piezoelectric element while securing stable ion generation by using the needle electrode, a high frequency of not less than 20 kHz is inevitably used. However, with this high frequency, a large amount of ozone is produced as a by-product, and due to heating, stable operation is difficult.

In a conventional needle-like ion generating electrode, influences from dust accumulation and wearing due to physical sputtering make it difficult to cause corona discharge, and the ion generation efficiency tends to be lowered. Also, in a ground electrode which is opposed to the needle-like ion generating electrode and provided for stabilizing discharge, due to electrostatic adsorption according to a high voltage and physical sputtering of the ion generating electrode, dust accumulates and the surface is contaminated, and these deteriorate the ion generation efficiency.

Therefore, a user must periodically perform maintenance for improving the ion generation efficiency by cleaning or replacing the pointed portion of the needle-like ion generating electrode and cleaning the ground electrode and the surroundings thereof. Such maintenance involves cleaning of the inside of a structure having the pointed portion, and as a high voltage is applied to this portion, the maintenance is dangerous and troublesome. An ionizer which includes a mechanism for cleaning has been also developed, however, this requires a complicated mechanism (refer to Patent Document 3).

On the other hand, an ion generating element (refer to Patent Documents 4 through 12) and ionizer which use a dielectric body having a discharge electrode and an induction electrode arranged on the surface as ion generating elements and are in plate shapes instead of needle shapes, has been developed (refer to Patent Document 11).

In the techniques shown in Patent Documents 4 through 11, local discharge is caused by applying a high voltage between a discharge electrode and an induction electrode via a dielectric body to generate ions, so that the element is in a flat shape that does not have a physically pointed structure. By providing a fine protrusion pattern on the discharge electrode, it becomes possible to generate both positive and negative ions stably by electric field concentration, and in comparison with the needle-like ion generating electrode, the same ion amount can be generated with a lower voltage and lower power consumption. Further, by providing a plurality of protrusions in the discharge electrode longitudinal direction, ions that are uniform in concentration can be one-dimensionally generated, so that the spatial variation of ion concentration of the needle-like ion generating electrode is reduced.

The element type electrode can generate ions at a low voltage, so that the electrode is hardly deteriorated and dust, etc., hardly adhere thereto, and in addition, ions are generated on the entire surface of the element, so that dust adhesion is dispersed, and as a result, the electrode is hardly contaminated. Even if it is contaminated, it does not have a pointed structure so that cleaning is easy, and, in comparison with the conventional needle-like electrode, maintenance performance is dramatically improved.

In the case where positive ions and negative ions are generated from an ion generating element by applying a high voltage to the above-described electrode structure formed via a dielectric body, a first problem is that the ion balance is lost due to disturbance factors, that is, deterioration of the electrode and efficiency lowering of the power supply. Herein, it is known that the ion concentration change in the atmosphere is expressed as in the following Equation 1 (for example, refer to "Relationship between ion life and aerosol concentration," Appendix 4, JIS B9929:2006).

$$\frac{dC_{ion}}{dt} = q - \alpha C_{ion}C_{ion} - \beta C_{ion}C_{aerosol} \qquad \text{Equation 1}$$

$C_{ion}$: positive or negative ion concentration
t: time
q: rate of ion generation
a: positive-negative ion recombination coefficient
b: attachment coefficient of ion to aerosol
$C_{aerosol}$: aerosol concentration Herein, when assuming that the third term of the right-hand side of Equation (1) can be ignored since the aerosol concentration is sufficiently low in a clean room or general manufacturing and indoor conditions, from Equation (1), the ion concentration change is balanced with the rate of ion generation by recombination of positive-negative ions.

In other words, when the rate of ion generation q increases, the ion concentration increases and the recombination rate of the second term of the right-hand side also increases to right the balance, so that a balanced value exists from which the ion concentration does not increase more. Therefore, at a generation rate equal to or more than this balanced condition, in principle, ions can be stably generated even if the ion generation amount slightly changes.

To obtain such stable ion generation, evaluation of the rate of ion generation q is important, however, it is difficult to obtain this theoretically. Therefore, conventionally, the voltage and frequency, etc., to be applied to the element-like electrode were arbitrarily determined by using a general-purpose power supply. For example, in Patent Documents 4 through 8, a continuous wave of a high voltage was applied, and for example, in Patent Document 4, an AC voltage of 2.5 $kv_{p-p}$ and a frequency of 50 kHz were determined, in Patent Document 5, a voltage of 1.9 to 3.25 $kv_{p-p}$ and a frequency of 5 kHz were determined, in Patent Document 6, a voltage of 2.6 to 6.7 kv$_{p-p}$ and a frequency of 40 kHz were determined, in Patent Document 7, a frequency of 100 to 900 Hz was determined, and in Patent Document 8, a voltage of 2 to 4 kV$_{p-p}$ and a frequency of 40 kHz were determined. These could not always realize stable ion generation.

Another problem in the ion generating element using the element-like electrode is that ozone is produced due to creeping discharge when a high-frequency high voltage is applied. That is, oxygen in the air is combined with atomic oxygen by plasma reaction on the creepage surface of the electrode to produce ozone. As an upper limit of the ozone concentration in the air, an allowable concentration of not more than 100 ppb in a working space is regulated (Japan Society for Occupational Health, Maximum Allowable Concentration Commission), and according to the humidity conditions and other operating conditions, 50 ppb, half the allowable concentration, is recommended. Conventionally, attempts were made to lower the ozone concentration by using a high voltage of an intermittent wave or pulsed wave which produces less ozone unlike the continuous wave (Patent Documents 9 through 12). However, in the case of pulse, generally, a power supply to which DC bias components are applied is used, so that, to separately generate positive and negative ions, at least one of each power supply is required, and downsizing of the device is difficult, and ion balance control is difficult. Specifically, the condition of Equation (1) is not spatially uniform, so that it is difficult to secure a stable ion balance. As partially described in Patent Document 12, there is an example in which the positive and negative ions are simultaneously generated by thinning out the sine waves of 100 Hz to about 60 Hz, however, this value is not always suitable for stable ion generation.

On the other hand, when a plate-like ion generating element is combined with an airflow generating mechanism such as a fan and used as an ionizer, improvement in ionization performance has been demanded. According to the EOS/ESD standards as international standards for ionizers, it is regulated that, when a plate monitor (metal plate) with a size of 150 mm×150 mm is charged, the time necessary to ionize it from a potential of 1000 V to 100 V is an ionization characteristic time $t_n$. Industrially, an ionization rate at which $t_n$ is 2 seconds or less at a distance of 30 cm is desirable, and this means that an object like a belt conveyor which operates at a rate of about 7.5 cm/sec can be continuously ionized. Herein, it is known that the ionization characteristic time is obtained from Equation (2), as a function of ion concentration and ion flow rate (for example, Equation (2) is true if Equation (4) described in J. M. Crowley, D. Leri, G. Dahlhoff and L. Vevit, J., Electrostatics., 61, p. 71-83 (2004) is simplified by assuming that ion current does not depend on an electric field).

$$t_n = \frac{C\Delta V}{uAC_{ion}e} \quad \text{Equation 2}$$

C: capacitance of ionization target
ΔV: potential difference of ionization target
u: ion velocity
A: area of ionization target
e: elementary charge (=1.6×10$^{-9}$)

Most of the conventional plate-like ion generating elements do not aim at ionization of object surfaces, so that ion generation conditions are not optimized. Therefore, it was difficult to obtain high-speed ionization performance with which $t_n$ of Equation (2) is 2 seconds or less.

Patent Document 1: Japan Patent Pre-Publication No. H04-94099
Patent Document 2: Domestic Re-publication of PCT International Publication No. WO2004/109875
Patent Document 3: Japan Patent Pre-Publication No. 2004-234972
Patent Document 4: Japan Patent Pre-Publication No. H08-82980
Patent Document 5: Japan Patent Pre-Publication No. 2002-365887
Patent Document 6: Japan Patent Pre-Publication No. 2004-103257
Patent Document 7: Japan Patent Pre-Publication No. 2005-328904
Patent Document 8: Japan Patent Pre-Publication No. 2006-222019
Patent Document 9: Japan Patent Pre-Publication 2003-249327
Patent Document 10: Japan Patent Pre-Publication No. 2006-59711
Patent Document 11: Japan Patent Pre-Publication No. 2006-196291
Patent Document 12: Japan Patent Pre-Publication No. 2006-260963

SUMMARY OF THE INVENTION

The inventors proposed the technique of Japanese Patent Application No. 2006-193697, etc., previously. As a result of further studies on the ion generator and ionizer using a fine electrode element that was the previously proposed technique, it became necessary to obtain optimal ranges of voltage, frequency, and airflow rate to realize more efficient ion generation, reduce ozone concentration as a by-product, and obtain higher-speed ionization performance as an ionizer, and realize an ion generator and an ionizer with higher performance.

Therefore, a first object of the present invention is to provide an ion generator which obtains stable ion generation even if the electrode and the power supply slightly change, satisfies voltage and frequency conditions for realizing an ozone concentration less than 50 ppb as an allowable concentration, and obtains a sufficient ion concentration without influences from environmental temperature and humidity. A second object of the present invention is to provide a high-performance ionizer with an ionization characteristic time of 2 seconds or less as a fan-type ionizer combining the above-described ion generator and an airflow generating mechanism.

The present invention for achieving the above-described objects is constituted as follows.

(1) A fan-type ion generator including a dielectric body, a discharge electrode having fine protrusions arranged on the surface of this dielectric body, and an induction electrode arranged on the back surface of the dielectric body, comprising:

an ion element in which by applying a sinusoidal AC high voltage to the discharge electrode, a potential difference from the induction electrode is generated, plasma is formed on the surface of the dielectric body, and positive ions, negative ions, and ozone are produced according to air ionization; and a fan which generates an airflow with respect to the discharge electrode, wherein the peak-to-peak voltage is not less than 3.5 kV and not more than 7 kV, the frequency f satisfies the following equation (7), and the relationship between the voltage V and the frequency f satisfies the following equation (10):

$$C_{ion}=C_{ion}{}^S-1.07\times10^6\exp(-K_{ion}f)\geq0.8\times10^6 \qquad \text{Equation 7}$$

$$C_{O_3}=F\times1.0\times10^{-4}\exp(V_{p\text{-}p}/1000)\leq50\text{ ppb} \qquad \text{Equation 10}$$

In the equations, $C_{ion}$: concentration of positive or negative ions, $C_{ion}{}^S$: balanced ion concentration, $K_{ion}$: extinction coefficient, $C_{O_3}$: ozone concentration.

(2) The fan-type ion generator according to the above (1), designed so as to satisfy the following formula 11 at a distance of 300 millimeters from the discharge electrode when the airflow rate is defined as u:

$$t_n=\frac{5\times10^6}{uC_{ion}}\leq \qquad \text{Equation 11}$$

In the equation, $t_n$: ionization characteristic time.

(3) A fan-type ionizer which performs ionization by using the fan-type ion generator according to the above (1) or (2).

According to the invention described in the above (1), in an ion generator having a fine electrode, the ion generator can be operated within optimal ranges of peak-to-peak voltage and frequency so that the operation is hardly influenced by the electrode and power supply changes and environmental temperature and humidity changes, and generates ions at a sufficient concentration, and realizes an ozone concentration of not more than the allowable value, so that sufficient ion generator performance is obtained while safety is secured.

Further, according to the invention described in the above (2), an ion generator can be supplied in which stable ion balance is secured even when exposed to slight disturbance factors when generated ions are conveyed by airflow.

According to the invention described in the above (3), use as an ionizer having sufficient ionization performance is possible by irradiating a charged target with ions generated from the ion generator.

BRIEF DESCRIPTION OF THE DRAWINGS

FIG. 9(A) is an assembly perspective view and FIG. 9(B) is an exploded perspective view.

DETAILED DESCRIPTION OF THE PREFERRED EMBODIMENTS

In the description given below, for convenience, the ion generator of the present invention is referred to as a first aspect of the invention, and an ionizer using this ion generator is referred to as a second aspect of the invention.

Figure 1:
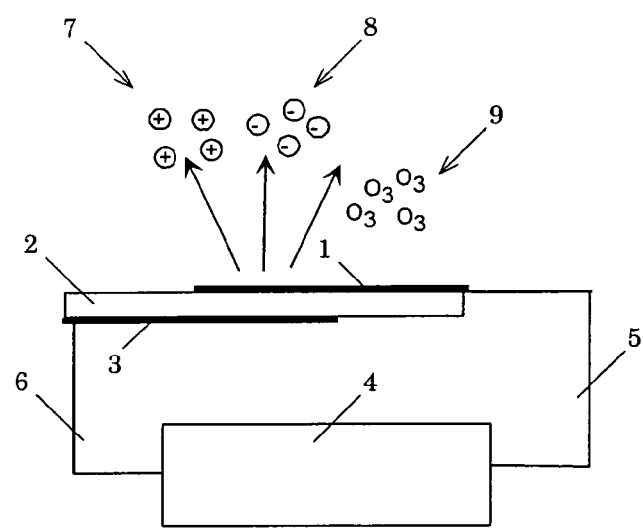
FIG. 1 is a constitutional view of an ion generator of the present invention.

First, the first aspect of the invention will be described with reference to the accompanying drawings. FIG. 1 shows an ion generator of the present invention. The ion generator 10 of the present invention includes a discharge electrode 1, a dielectric body 2, an induction electrode 3, and a power supply 4, and by fine machining, the discharge electrode 1 is formed on the surface of the dielectric body 2, and the induction electrode 3 is formed on the back surface. A sinusoidal AC high voltage is applied to the discharge electrode 1 via voltage lead wires 5 and 6, and a potential difference from the induction electrode 3 is provided, whereby plasma is formed on the surface of the dielectric body 2, and by air ionization, positive ions 7, negative ions 8, and ozone 9 are produced.

Figure 2:
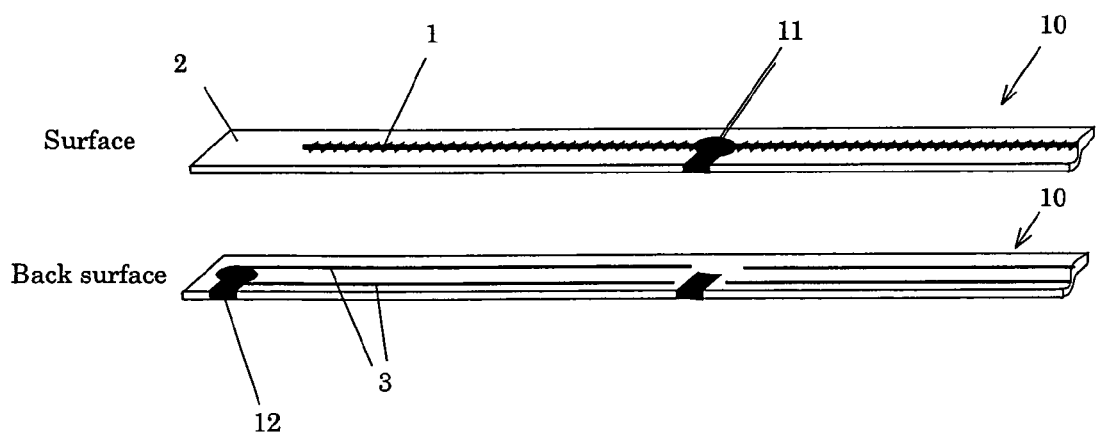
FIG. 2 is a structural view of an ion generating element of the present invention.

As details of the ion generating element 10, as shown in FIG. 2, it can be connected to a power supply without fail by a discharge electrode contact 11 and an induction electrode contact 12 as shown in FIG. 2. On the discharge electrode 1, fine protrusions are provided at intervals so as not to overlap with a projected line of the induction electrode 3 so that plasma is formed locally.

Figure 3:
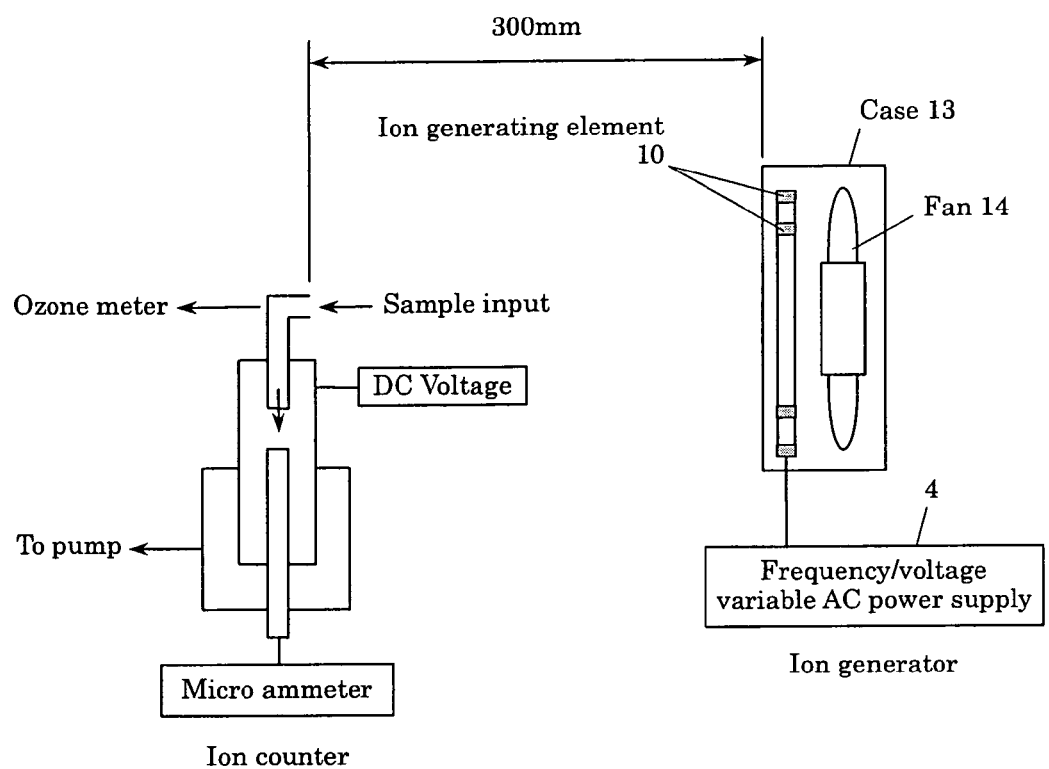
FIG. 3 is an explanatory view of a system for measuring ion concentration and ozone concentration.

FIG. 3 shows a system for measuring ion concentration. The ion generating element 1 of FIG. 2 was machined into a ring shape and housed in a box-shaped case 13, and a fan 14 was installed therein to form an ion generator. As a power supply, a power supply 4 whose frequency and voltage could be arbitrarily set was used, and ions were generated and transported by changing these parameters. For measuring the ion concentration, as shown in FIG. 3, an ion counter set at a distance of 300 mm from the center of the ion generator was used. Ion electrostatic repulsion was caused by applying a DC voltage of about 30V to the outer cylindrical portion, and from a current value measured with a micro ammeter connected to the central electrode, an ion concentration was calculated by using the following Equation (3).

$$C_{ion}=\frac{I_{ion}}{eQ} \qquad \text{Equation 3}$$

$I_{ion}$: ion current value

Q: flow rate

Figure 4:
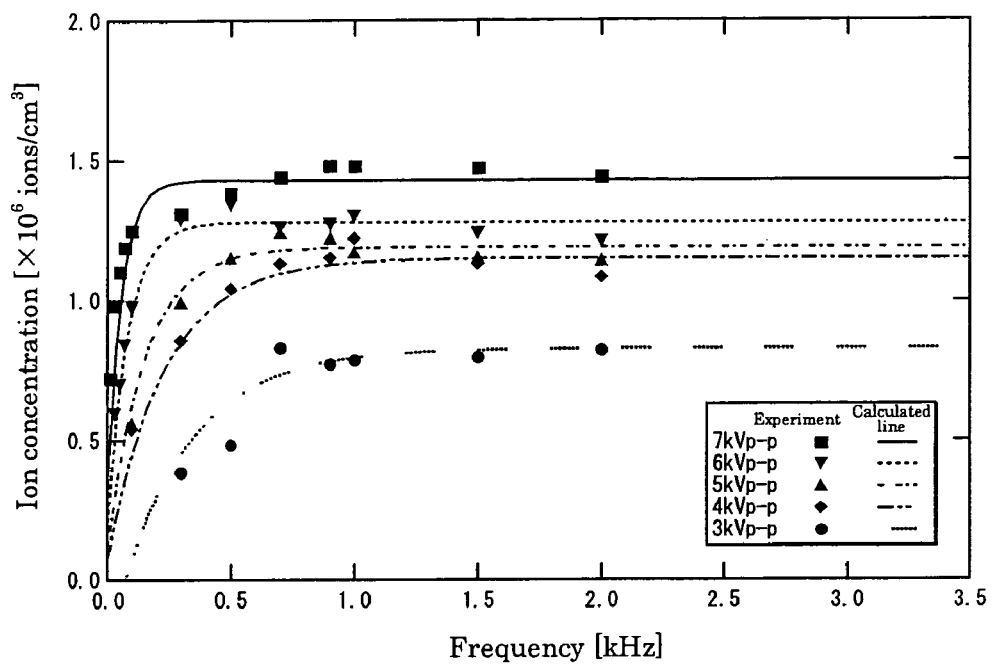
FIG. 4 is a graph showing frequency characteristics of ion concentration.

The results of plotting of ion concentrations thus measured with respect to the frequencies in the range of peak-to-peak voltage $V_{p\text{-}p}$ of 3 to 7 kV applied to the discharge electrode are shown in FIG. 4. It was experimentally proved that depending on the voltage applied, the ion concentration increased with respect to the frequency, and became constant at a specific frequency or more. Herein, it was found that, when the ion concentration that becomes constant was defined as a balanced ion concentration at each voltage, the higher the voltage, the higher the balanced ion concentration, and the higher the voltage, the lower the frequency reaching the balanced ion concentration. As for this type of phenomenon, the balance between the ion generation rate and the extinction rate according to recombination of positive and negative ions shown in Equation 1 is related.

It is known that the ion recombination shown by the second term of the right-hand side of Equation 1 attenuates exponentially (Appendix 4, JIS B9929:2006). Therefore, when the balanced ion concentration is defined as $C_{ion}^S$, the ion concentration is expressed approximately by Equation (4) as a function of frequency.

$$C_{ion}=C_{ion}^S-1.07\times 10^6\exp(-K_{ion}f) \quad \text{Equation 4}$$

$K_{ion}$: extinction coefficient
f: frequency

By fitting the experimental results of FIG. 4 by using Equation (4), as the balanced ion concentration and extinction coefficient, the values shown in Table 1 were obtained.

TABLE 1

Balanced ion concentration and extinction coefficient

| $V_{p-p}$ [kV] | $C_{ion}^S$ [×10⁶ cm⁻³] | $K_{ion}$ [—] |
|---|---|---|
| 3.0 | 0.827 | 0.0350 |
| 4.0 | 1.15 | 0.0426 |
| 5.0 | 1.19 | 0.0653 |
| 6.0 | 1.28 | 0.12 |
| 7.0 | 1.43 | 0.17 |

Figure 5:
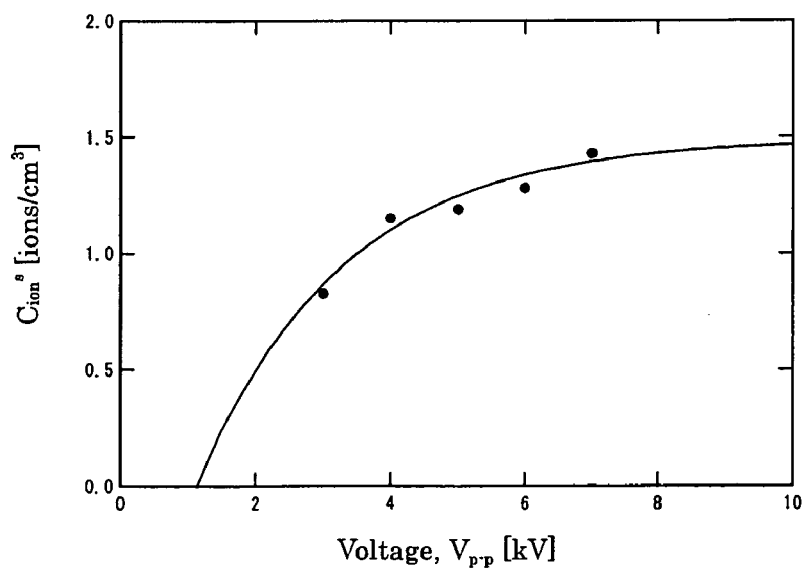
FIG. 5 is a graph showing voltage dependency of balanced ion concentration.
Figure 6:
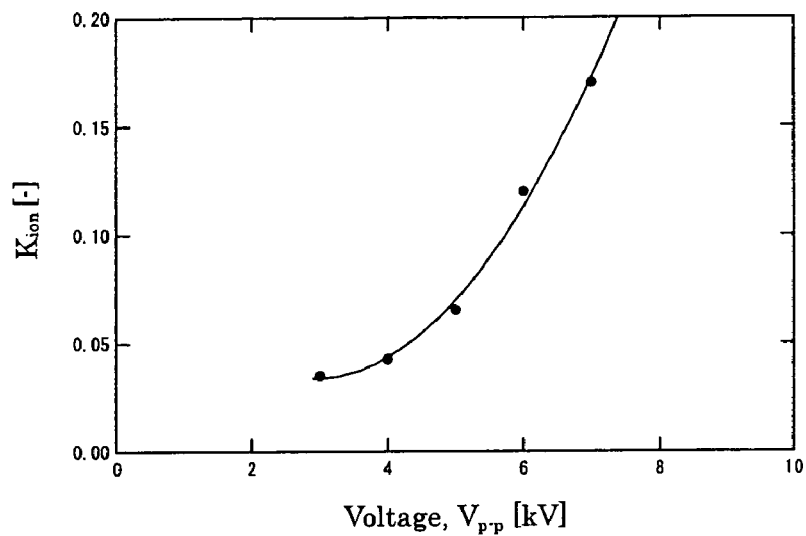
FIG. 6 is a graph showing voltage dependency of extinction coefficient.

From the results of FIG. 4, the calculated lines obtained by using Equation (4) satisfactorily fit the experimental values at any voltage in the range of this experiment, so that it is confirmed that Equation (4) properly expresses the frequency characteristic of the ion concentration. Herein, the balanced ion concentration $C_{ion}^S$ [cm⁻³] and extinction coefficient $K_{ion}$ [—] of Table 1 can be further approximated by the following experimental equations (5) and (6) as functions of the peak-to-peak voltage (FIG. 5 and FIG. 6).

$$C_{ion}^S=1.49\times 10^6-2.54\times 10^6\exp(-0.459\times 10^{-3}V_{p-p}) \quad \text{Equation 5}$$

$$K_{ion}=0.105-4.87\times 10^{-5}V_{p-p}+8.34\times 10^{-9}V_{p-p}^2 \quad \text{Equation 6}$$

$(V_{p-p} \geq 3000 V)$

Herein, at a peak-to-peak voltage of 3 kV or less, for example, at 2.9 kV, the ion concentration did not reach the balanced value. For application to ionization described later, an ion concentration of not less than $8\times 10^5$ ions/cm³ is necessary. Therefore, first, a minimum frequency satisfying the following equation (7) was defined as a minimum frequency $f_{min}$, and this value was obtained as shown in Table 2.

$$C_{ion}=C_{ion}^S-1.07\times 10^6\exp(-K_{ion}f)\geq 0.8\times 10^6 \quad \text{Equation 7}$$

TABLE 2

Minimum frequency at each voltage

| $V_{p-p}$ [kV] | $f_{min}$ [Hz] |
|---|---|
| 3.0 | 1085 |
| 4.0 | 280 |
| 5.0 | 175 |
| 6.0 | 70 |
| 7.0 | 35 |

Within the range shown in Table above, sufficient ion generation is obtained, however, under conditions below the balanced ion concentration, the ion concentration greatly changes due to disturbance factors such as variation of frequency and voltage and deterioration of the element, etc., so that stable ion generation cannot be obtained. Therefore, it is preferable that the operation is performed under conditions of not less than the balanced frequency $f^S$ [Hz] (frequency at which ion concentration is 99% of balanced ion concentration) shown in Table 3 below.

TABLE 3

Balanced frequency at each voltage

| $V_{p-p}$ [kV] | $f^S$ [Hz] |
|---|---|
| 3.0 | 1400 |
| 4.0 | 1070 |
| 5.0 | 700 |
| 6.0 | 370 |
| 7.0 | 250 |

Figure 7:
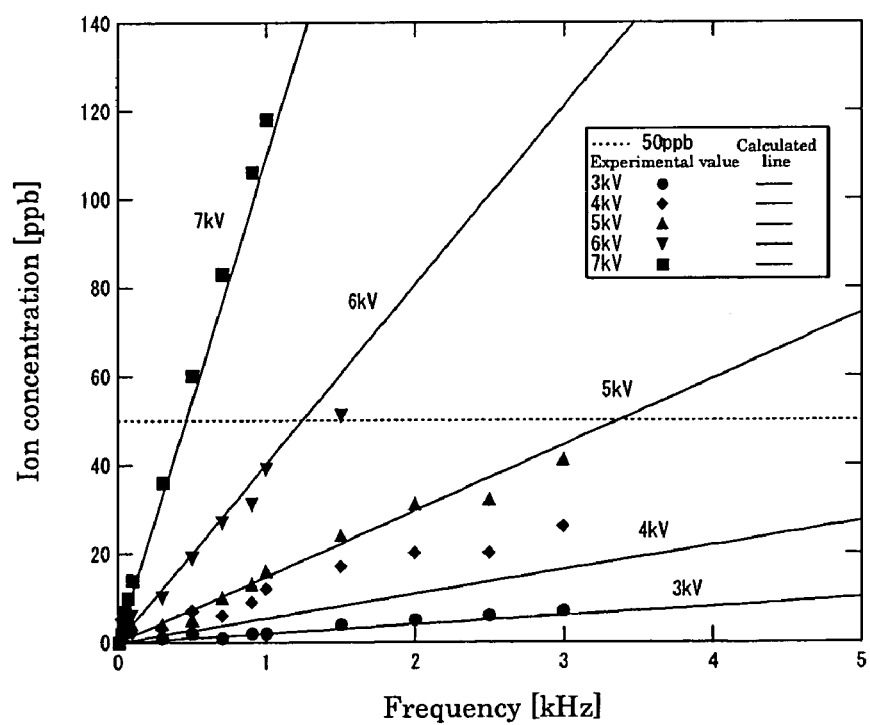
FIG. 7 is a graph showing frequency characteristic of ozone concentration.

Next, the results of measurement of ozone concentration as a function of the frequency by using the system of FIG. 3 are shown in FIG. 7. In a low concentration range of not more than 0.1 ppm, extinction according to recombination as in the case of the ion concentration does not occur, so that the ozone concentration $C_{O3}$ [ppb] is obtained by the following equation simply in proportion to the frequency f.

$$C_{O_3}=K_{O_3}f \quad \text{Equation 8}$$

Herein, the coefficient $K_{O3}$ is a function of the applied voltage $V_{p-p}$ and in the electrode form and experimental range of the present invention, the relationship of the following equation (9) was obtained experimentally.

$$K_{O_3}=1.0\times 10^{-4}\exp(V_{p-p}/1000) \quad \text{Equation 9}$$

As shown in FIG. 7, comparing the calculated values obtained from the equation shown above and the experimental values, these coincide well with each other at any voltage and frequency in the range of this experiment, and it is proved that Equations (8) and (9) well express the frequency characteristic of the ozone concentration.

From the description above, the relationship between the voltage V and the frequency f that allow the regulated value of 0.05 ppm (50 ppb) in the working environment [at a distance of 300 mm from the ion generating section (discharge electrode)] is expressed by the following equation (10).

$$C_{O_3}=f\times 1.0\times 10^{-4}\exp(V_{p-p}/1000)\leq 50 \text{ ppb} \quad \text{Equation 10}$$

From the relationship of the equation shown above, the maximum frequencies $f_{max}$ as allowable limit values at the respective voltages are summarized in the following table.

TABLE 4

Maximum frequency at each voltage

| $V_{p-p}$ [kV] | $f_{max}$ [Hz] |
|---|---|
| 3.0 | 24900 |
| 4.0 | 9160 |
| 5.0 | 3350 |
| 6.0 | 1200 |
| 7.0 | 450 |

Figure 8:
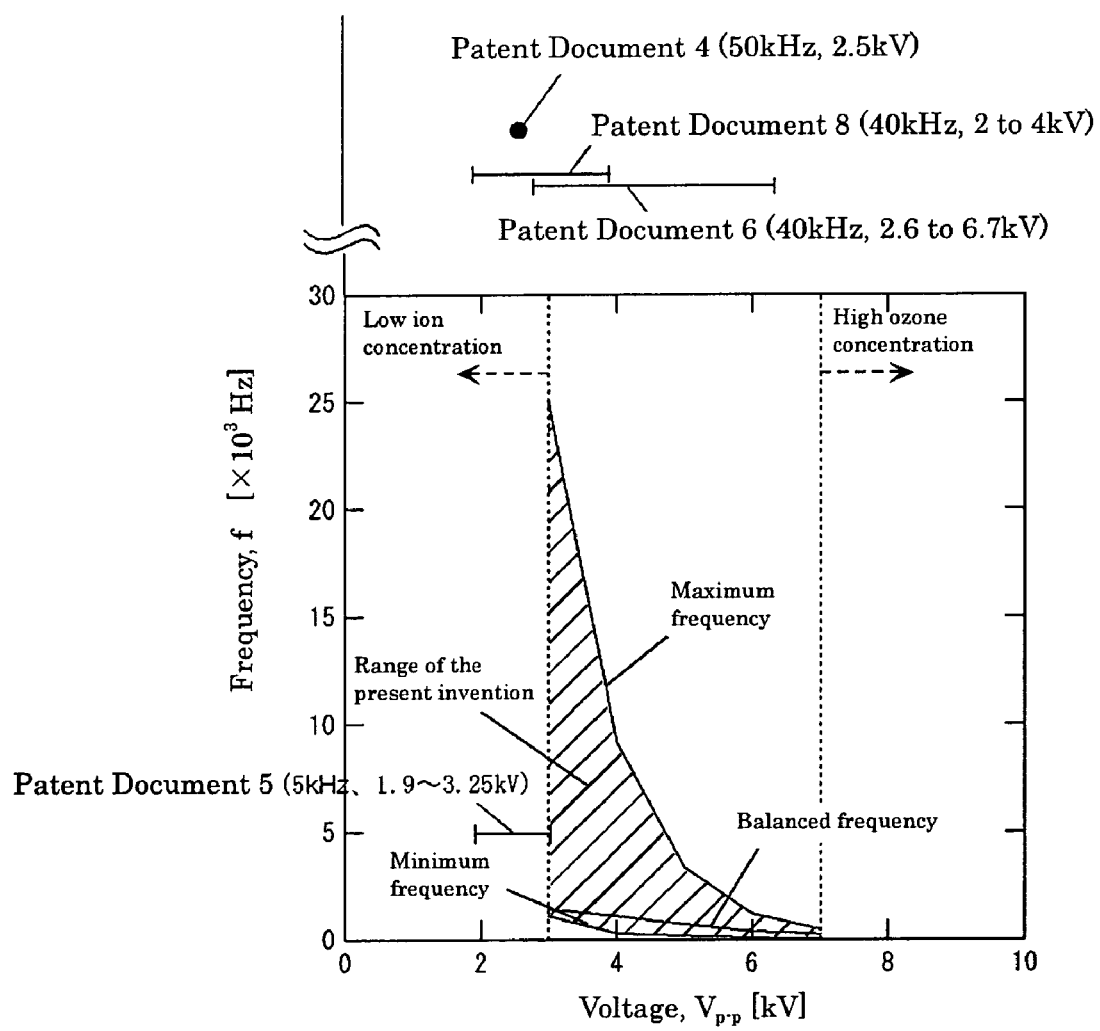
FIG. 8 is a graph showing a voltage range (shaded) before considering the humidity influence on the ion concentration of the present invention.

From the description given above, the minimum frequency, the balanced frequency, and the maximum frequency at each voltage are summarized in Table 5. The range of these is illustrated in FIG. 8 as the range of the present invention. At a peak-to-peak voltage less than 3.0 kV, the ion concentration does not reach the balanced ion concentration, and further, the frequency becomes very high, so that this is not practicable. If the voltage is more than 7 kV, the ozone concentration immediately exceeds the allowable value, so that this is not practicable. In addition, according to the low frequency, temporal fluctuation of positive and negative ion concentrations comes into question. Therefore, when assuming that there is no influence from the humidity, the range of the first aspect of the invention is a range in which the peak-to-peak voltage is not less than 3.0 kV and not more than 7 kV and the frequency satisfies Equations 7 and 10, and more preferably, a frequency range in which the balanced ion concentration is reached.

TABLE 5

Summary of parameter ranges at each voltage

| $V_{p-p}$ [kV] | $f_{min}$ [Hz] | $f^S$ [Hz] | $f_{max}$ [Hz] | $\frac{C_{ion}^S}{[\times 10^6 \text{ cm}^{-3}]}$ |
|---|---|---|---|---|
| Less than 3.0 | (Comparative) Stable ion generation is not obtained at any frequency. | | | |
| 3.0 | 1085 | 1400 | 24900 | 0.827 |

(=15×15 cm) as ionization conditions using a standard charge plate monitor into the Equation 2, the following Equation 11 is obtained.

$$t_n = \frac{5 \times 10^6}{uC_{ion}} \quad \text{Equation 11}$$

An average flow rate of a standard fan to be attached to a fan-type ionizer is about 3 m/s at most, and to set $t_n$ to 2 seconds or less by only the airflow, from Equation 11 shown above, an ion concentration of not less than $0.8 \times 10^6$ [cm$^{-3}$] is necessary. This coincides with the ion concentration at the minimum frequency described above.

An influence from humidity is one of the disturbance factors in ion generation. Particularly, to determine the lower limit of ion generation, the humidity influence on the ion concentration was considered, and the results shown in Table 6 were obtained.

TABLE 6

| Frequency (kHz) | Number of positive ions (n/cc) Humidity (%) | | | | Number of negative ions (n/cc) Humidity (%) | | | |
|---|---|---|---|---|---|---|---|---|
| | 10 | 50 | 60 | 70 | 10 | 50 | 60 | 70 |
| Applied voltage: 3.0 kVpp (comparative) | | | | | | | | |
| 1.085 | 8.0E+05 | 4.3E+05 | 4.4E+05 | 2.6E+05 | 8.7E+05 | 4.6E+05 | 3.7E+05 | 2.6E+05 |
| 1.40 | 7.9E+05 | 5.8E+05 | 5.0E+05 | 5.8E+05 | 9.0E+05 | 5.0E+05 | 4.5E+05 | 6.4E+05 |
| 2.00 | 7.7E+05 | 5.6E+05 | 5.3E+05 | 5.2E+05 | 8.6E+05 | 6.1E+05 | 5.6E+05 | 4.0E+05 |
| Applied voltage: 3.3 kVpp (comparative) | | | | | | | | |
| 1.085 | 8.8E+05 | 8.4E+05 | 8.1E+05 | 4.1E+05 | 9.3E+05 | 7.1E+05 | 6.7E+05 | 5.7E+05 |
| 1.40 | 9.0E+05 | 7.8E+05 | 7.9E+05 | 8.7E+05 | 9.6E+05 | 8.1E+05 | 6.6E+05 | 7.0E+05 |
| 2.00 | 9.2E+05 | 8.8E+05 | 7.1E+05 | 8.4E+05 | 9.0E+05 | 8.8E+05 | 8.2E+05 | 7.8E+05 |
| Applied voltage: 3.5 kVpp (the present invention) | | | | | | | | |
| 1.085 | 1.1E+06 | 8.8E+05 | 9.3E+05 | 8.5E+05 | 1.1E+06 | 8.8E+05 | 8.2E+05 | 8.2E+05 |
| 1.40 | 1.1E+06 | 8.9E+05 | 8.8E+05 | 8.8E+05 | 1.0E+06 | 9.3E+05 | 9.3E+05 | 9.5E+05 |
| 2.00 | 1.1E+06 | 1.0E+06 | 9.5E+05 | 9.0E+05 | 1.0E+06 | 9.7E+05 | 8.9E+05 | 9.1E+05 |

TABLE 5-continued

Summary of parameter ranges at each voltage

| $V_{p-p}$ [kV] | $f_{min}$ [Hz] | $f^S$ [Hz] | $f_{max}$ [Hz] | $\frac{C_{ion}^S}{[\times 10^6 \text{ cm}^{-3}]}$ |
|---|---|---|---|---|
| 4.0 | 280 | 1070 | 9160 | 1.15 |
| 5.0 | 175 | 700 | 3350 | 1.19 |
| 6.0 | 70 | 370 | 1200 | 1.28 |
| 7.0 | 35 | 250 | 450 | 1.43 |
| More than 7.0 | (Comparative) Ozone concentration is always not less than 50 ppb at any frequency. | | | |

Figure 9:
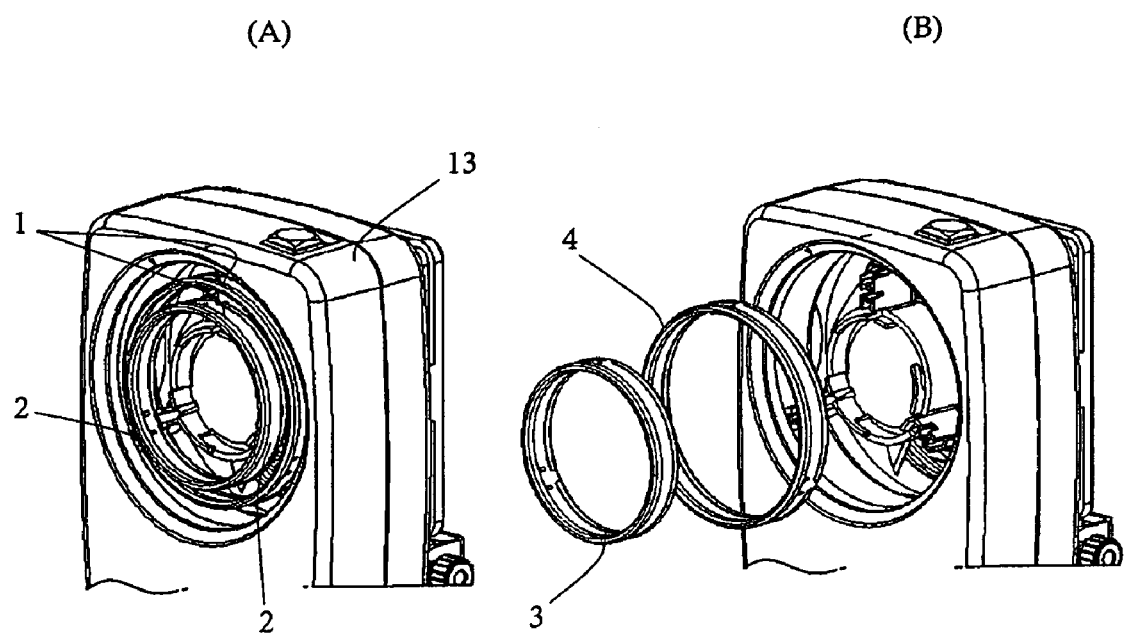
FIG. 9 are constitutional views showing attachment of an ion generating element to an ionizer.
Figure 10:
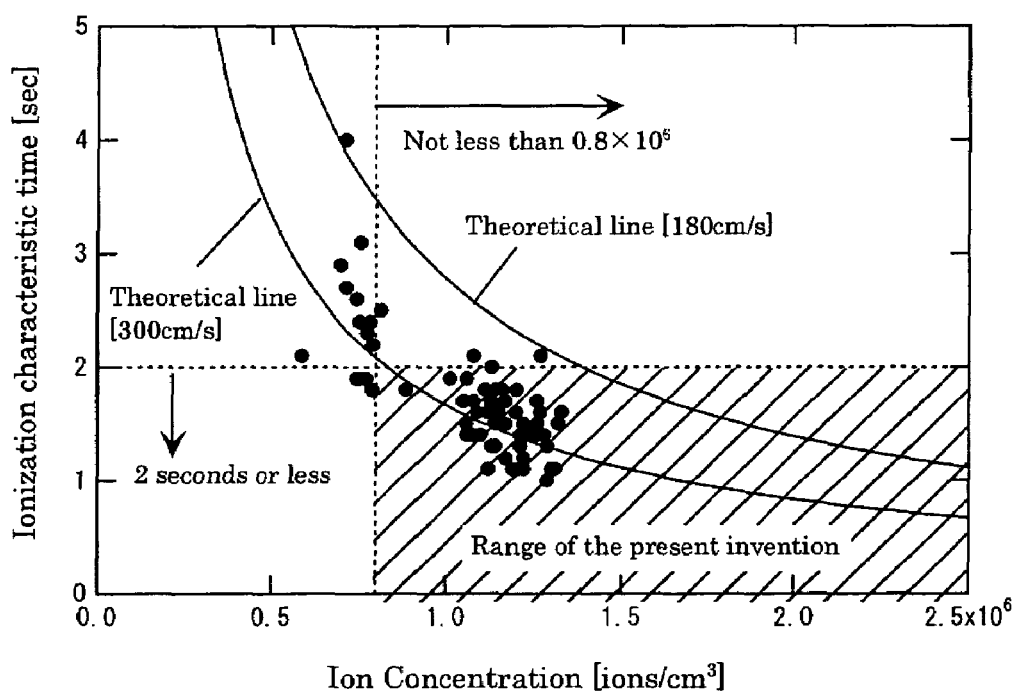
FIG. 10 is a graph showing an ion concentration range before considering the influence of humidity on the ion concentration of the present invention.

Next, an embodiment of the second aspect of the invention will be described with reference to the drawings. The ion generator shown in FIG. 3 includes a fan, a plate-like ion generating element 10, and a power supply 4, and can be used as an ionizer. In detail, an ionizer structured so that a ring-shaped element is housed in a cylindrical case 4 as shown in FIG. 9 shows the most excellent performance.

To determine the ionizer operating conditions, by assigning C=20 pF, DV=900V (=1000V−100V), and A=225 cm$^2$ In Table 6, at the applied voltage of 3 kVpp as a comparative example, an ion concentration of not less than $0.8 \times 10^6$ [cm$^{-3}$] as a set value at a low humidity (Rh 10%) is almost obtained, however, at a high humidity of 50% or more, the ion concentration lowers. At the applied voltage of 3.3 kV as another comparative example, ion concentration lower than the set value was also observed at some high humidities. On the other hand, at 3.5 kVpp in the range of the present invention, sufficient ion concentration is obtained in any humidity range of 10 to 70%.

What is claimed is:
1. A fan-type ion generator including a dielectric body, a discharge electrode having fine protrusions arranged on the surface of this dielectric body, and an induction electrode arranged on the back surface of the dielectric body, comprising:
    an ion element in which by applying a sinusoidal AC high voltage to the discharge electrode, a potential difference from the induction electrode is generated, plasma is formed on the surface of the dielectric body, and positive ions, negative ions, and ozone are produced according to air ionization; and a fan which generates an airflow with respect to the discharge electrode, wherein the peak-to-peak voltage is not less than 3.5 kV and not more than 7 kV, the frequency f satisfies the following equation 7, and the relationship between the voltage V and the frequency f satisfies the following equation 10:

$$C_{ion} = C_{ion}^{S} - 1.07 \times 10^6 \exp(-K_{ion} f) \geq 0.8 \times 10^6 \qquad \text{Equation 7}$$

$$C_{O_3} = f \times 1.0 \times 10^{-4} \exp(V_{p\text{-}p}/1000) \leq 50 \text{ ppb} \qquad \text{Equation 10}$$

In the equations, $C_{ion}$: concentration of positive or negative ions, $C_{ion}^{s}$: balanced ion concentration, $K_{ion}$: extinction coefficient, $C_{O_3}$: ozone concentration.

2. The fan-type ion generator according to claim 1, designed so as to satisfy the following formula (11) at a distance of 300 millimeters from the discharge electrode when the airflow rate is defined as u:

$$t_n = \frac{5 \times 10^6}{u C_{ion}} \leq 2 \text{ seconds} \qquad \text{Equation 11}$$

In the equation, $t_n$: ionization characteristic time.

3. A fan-type ionizer which performs ionization by using the fan-type ion generator according to claim 1.

* * * * *